United States Patent
Holerca et al.

(10) Patent No.: US 6,969,510 B2
(45) Date of Patent: Nov. 29, 2005

(54) GLYCINE-FREE ANTIPERSPIRANT SALTS WITH BETAINE FOR ENHANCED COSMETIC PRODUCTS

(75) Inventors: Marian Holerca, Somerset, NJ (US); Xiaozhong Tang, Bridgewater, NJ (US); Heng Cai, Yardley, PA (US)

(73) Assignee: Colgate-Palmolive Company, New York, NY (US)

( * ) Notice: Subject to any disclaimer, the term of this patent is extended or adjusted under 35 U.S.C. 154(b) by 0 days.

(21) Appl. No.: 10/462,200

(22) Filed: Jun. 16, 2003

(65) Prior Publication Data
US 2004/0204601 A1 Oct. 14, 2004

Related U.S. Application Data

(63) Continuation-in-part of application No. 10/406,856, filed on Apr. 4, 2003, now abandoned.

(51) Int. Cl.$^7$ .............................. A61K 7/34; A61K 7/38; C07F 7/28; C07F 5/06
(52) U.S. Cl. .............................. 424/65; 424/66; 424/68; 556/56; 556/183
(58) Field of Search .............................. 424/65, 66, 68; 556/56, 183

(56) References Cited

FOREIGN PATENT DOCUMENTS

GB          1 479 132          *  7/1977

* cited by examiner

Primary Examiner—Porfirio Nazario-Gonzalez
(74) Attorney, Agent, or Firm—Rosemary Miano

(57) ABSTRACT

A glycine-free aluminum and/or zirconium Betaine salt having a metal to chloride molar ratio in the range of 0.3–2.5:1, a Betaine:aluminum molar ratio in the range of 0.05–1.0:1 and/or a Betaine:zirconium molar ratio in the range of 0.2–3.0:1, wherein the Betaine is used in its normal form described in Formula I, or in its derivative form of Betaine hydrochloride, described in Formula IA:

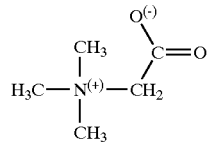

Formula I

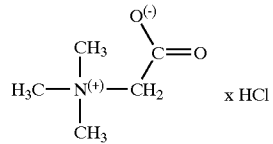

Formula IA

12 Claims, No Drawings

GLYCINE-FREE ANTIPERSPIRANT SALTS WITH BETAINE FOR ENHANCED COSMETIC PRODUCTS

This application is a continuation-in-part of U.S. Ser. No. 10/406,856, filed Apr. 4, 2003, now abandoned.

FIELD OF THE INVENTION

This invention relates to a class of glycine-free antiperspirant salts combined with Betaine as defined below or its hydrochloride form that may be used to formulate antiperspirants with enhanced stability and efficacy.

BACKGROUND OF THE INVENTION

A variety of art is available that describes various salts and methods of making them.

U.S. Pat. No. 4,331,609 to Orr teaches an antiperspirant active comprising aluminum and zirconium made with separate aluminum and zirconium compounds as well as a neutral amino acid wherein the molar ratio of neutral amino acid to total metal is from about 0.90 to about 0.24. The total metal:chlorine ratio in the complex that is formed is less than 1.30.

EP publication number 0 047 650 describes aqueous solution-stable antiperspirant complexes comprising an aluminum compound, a zirconium or hafnium compound, a water soluble neutral amino acid and an inorganic acid. The molar ratio of neutral amino acid to total metal is from about 0.90 to about 0.24 in an aqueous system, and the molar ratio of neutral amino acid to total metal is from about 0.90 to about 0.75 in a non-aqueous system. The total metal:chlorine ratio in the complex that is formed is less than 1.30.

United Kingdom Patent Application GB 2,076,289 describes an antiperspirant compositions comprising a combination of an aluminum chloride and an aluminum zirconium hydroxychloride in a synergistic mixture. The metal:chloride ratio is less than 0.9.

Canadian Patent 1,153,313 describes an antiperspirant composition which contains a buffering agent such as glycine with a synergistic mixture of aluminum chlorohydrate, aluminum chloride or aluminum zirconium polychlorohydrate complex. The molar ratio of aluminum to chloride is in the range of 0.78:1 to abut 1.95:1. Various salts are described which have a metal:halide ratio of 2.1:1–0.9:1. The glycine:zirconium ratio is much less than 1:1.

U.S. Pat. No. 4,871,525 to Giovanniello et al describes a solid powder of aluminum zirconium hydroxyl halide glycinate complex having improved antiperspirant activity wherein the glycine is used to prevent gel formation. The ratio of Zr to glycine is less than 1:1.

U.S. Pat. No. 6,126,928 to Swaile describes antiperspirant compositions wherein the molar ratio of neutral amino acid to total metal (aluminum+zirconium) is from about 0.90 to about 0.24, and the mole ratio of (aluminum+zirconium):chlorine is less than about 1.30:1.

U.S. Pat. No. 6,066,314 to Tang describes the use of post added glycine to aluminum zirconium salts in an amount in the range of 1:1.2–1:5 of zirconium:amino acid on a weight::weight basis.

None of the above cases described the combination of metal to chloride in combination with the Betaine (as defined herein) to zirconium ratio as found in the instant invention. Thus, it is surprising that the antiperspirant actives described in this invention provide more efficacious cosmetic products.

The term "betaine" is used in a variety of ways. In particular, a variety of uses of betaines with long chains can be found in the surfactant art. Such betaines may be represented by the following Formula A where n>0:

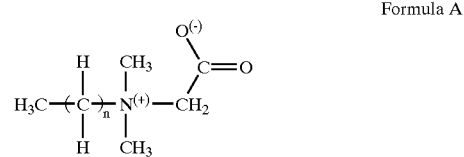

Formula A

The methyl groups can be replaced with other longer chain alkyls and can be straight chain or branched.

The Betaine (defined below) of this invention, however, is not a surfactant and has been found to have properties important to the field of antiperspirant salts that contain zirconium. The Betaine used in this invention is a natural product found in a number of plants in the Chenopodiaceae family, and also in fish and selected legumes. Extracted most often from sugar beets (*Beta Vulgaris*), it is reported as an extremely versatile molecule with a wide range of applications: food supplement, anti-irritant, skin moisturizer, skin-softening agent, skin-conditioning agent, promoter of wound healing and component in cosmetic compositions for skin aging and stressed skin.

Betaine in IUPAC nomenclature is 1-carboxy-N,N,N-trimethylmethanaminium hydroxide-inner salt, with alternative names including carboxymethyl-trimethyl-ammonium betaine or (carboxymethyl)trimethylammonium hydroxide-inner salt or glycine betaine or glycoll betaine or glycyl betaine or trimethyl glycine or trimethylglycoll. For convenience here the material of Formula I ($C_5H_{11}NO_2$; Mass= 117.08 amu; molecular weight=117.15; analysis as C: 51.26; H: 9.46; N: 11.96; O: 27.32) will be referred to as Betaine.

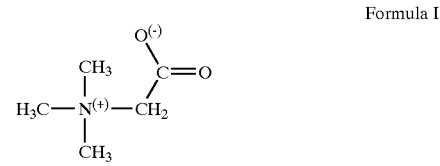

Formula I

The hydrochloride form is also included in the scope of this invention. The hydrochloride form may be represented by Formula IA:

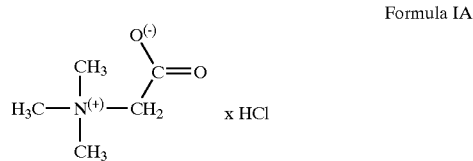

Formula IA

Betaine appears in numerous patents, with a wide range of applications.

Note that for purposes of this application, the term "betaine" will be used if any compound of Formula A is described. The term "Betaine" will be used if a compound of Formula I is described. The term "Betaine hydrochloride" will be used if a compound of Formula IA is described.

PCT Publication WO 00/67726 describes host-guest processes and formulations containing Betaine for delivering bio-affecting compounds and topical compositions for cosmetic or pharmaceutical uses formed by the processes. The processes comprise mixing, in any order: (i) a nonionic surfactant; (ii) an amphoteric surfactant; (iii) a solvent for the amphoteric surfactant; (iv) an aromatic compound; (v) an aluminum cation; (vi) a Lewis acid that is not a Bronsted-Lowry acid; and (vii) a Bronsted-Lowry acid.

U.S. Pat. No. 5,877,143 describes a composition containing a lamellar liquid crystalline phase which comprises betaines and amine oxides. This is a pumpable, fluid composition of amine oxide, betaine and/or sultaine is prepared with active concentration of about 36–45% of these materials by the addition of alkaline earth or aluminum salts.

German Patent DE 19725087 is related to cosmetic and dermatologic oil-in-water emulsion formulations for light protection containing hydrophobic inorganic micropigments and hydrophilic surfactants.

PCT Publication WO 97/23594 describes skin cleansing compositions with enhanced antimicrobial activity comprising 0.1–30% of an amphoteric, zwitterionic, nonionic, anionic and/or cationic emulsifier, 0.00001–5% of a Ag compound (AgCl, $Ag_2CO_3$, etc.), deposited on a particulate inert support material (metal oxides, especially $TiO_2$) as antimicrobial agent, and $H_2O$. A typical composition contains cetyl betaine.

Japanese Patent JP 52093633 describes chemical polishing solutions for aluminum and its alloys. Al or its alloys are chemically polished in a $H_3PO_4$—$H_2SO_4$ solution containing a betaine and organic polythio sulfonic acid salt.

British Patent GB 2354771 relates to bactericide combinations in detergents. The detergent comprises a bactericide in combination with an anionic, cationic, nonionic or amphoteric surfactant which has a C12–18 alkyl group as the longest chain attached to the hydrophilic moiety.

Japanese Patent JP 2001163752 describes long-lasting cosmetic makeup compositions comprising plate-type glossy polymer powders and antiperspirants.

European Patent EP 1005853 describes the use of betaines as antiperspirants. Mono-, di-, and trimethylammonio-substituted carboxylic acids $(R^1)(R^2)(R^3)N^+$—$(CH_2)_nC(O)O$— (with $R^1$-$R^3$=H, Me; n=1–10) are active as antiperspirants and are compatible with the skin and with other conventional constituents of antiperspirant and deodorant compositions.

European Patent EP 1005852 describes the use of functionally substituted betaines as antiperspirants. Mono-, di-, and trimethylammonio-substituted carboxylic acids $R^1R^2R^3N+(CH_2)_nCHX(CH_2)_mC(O)O$— and/or $X(CH_2)_nCH(N+R^1R^2R^3)(CH_2)_mC(O)O$— ($R^1$-$R^3$=H, Me; m, n=1–8 are active as antiperspirants and are compatible with the skin and with other conventional constituents of antiperspirant and deodorant compositions.

Japanese Patent JP 11130652 discloses skin-conditioning and moisturizing cosmetics containing clay minerals and low-molecular-weight betaines to inhibit the release of pyrrolidonecarboxylic acid (a natural moisturizing factor) from human skin.

German Patent DE 2610225 describes aluminum salts of Betaine chloride being useful as ulcer inhibitors, for treatment of gastritis, to promote wound healing, and as antiperspirants and deodorants.

PCT Publication WO 01/62222 describes cosmetic compositions containing phospholipids and quaternary amines. The invention relates to a cosmetic composition, especially for use on aging and/or stressed skin, the composition comprising, in addition to water, at least one substance that forms lamellar structures with water. Compositions including Betaine are described.

PCT Publication WO 01/47479 assigned to the same owner as this case describes cosmetic moisturizing compositions containing quaternary ammonium compounds. Compositions with cocamidopropyl betaine are described.

PCT Publication WO 01/39730 describes a cosmetic composition containing peat and Betaine.

PCT Publication WO 97/46246 is related to complex preparations for topical use containing Betaine to stimulate cellular and physiological processes.

PCT Publication WO 91/18588 presents a method of reducing the irritating properties of a cosmetic composition by addition of Betaine derivatives.

Japanese Patent JP 03033266 describes modified fabrics coated with a mixture of dodecyl betaine and other ingredients for controlling pH change in skin during sweating.

BRIEF SUMMARY OF THE INVENTION

This invention comprises aluminum and/or zirconium salts with Betaine as a complexing agent and buffering agent and which do not contain glycine. Betaine can be used in its normal form or as Betaine hydrochloride.

DETAILED DESCRIPTION OF THE INVENTION

This invention comprises glycine-free aluminum and/or zirconium Betaine salts having a metal to chloride molar ratio in the range of 0.3–2.5:1 (especially in the range of 0.9–2.1:1), a Betaine:aluminum molar ratio in the range of 0.05–1.0:1 (particularly 0.05–0.26:1 and, more particularly, 0.05–0.16:1) and/or a Betaine:zirconium molar ratio in the range of 0.2–3.0:1 (particularly 0.4–1.5:1).

The salts of this invention may be made in a variety of ways:

Method A: An aluminum chlorohydrate (ACH) solution of ACH salt in water of suitable concentration is mixed with an aqueous solution of zirconyl chloride ($ZrOCl_2$) (or alternatively combining $ZrOCO_3$ and HCl to make the zirconyl chloride in situ) of suitable concentration and powdered Betaine. The mixture is stirred at room temperature to obtain the salt, or dried to remove water to come out with powder form of the salt.

Method B: A suitable commercially available glycine-free aluminum zirconium tetrachlorohydrex salt, aluminum zirconium trichlorohydrex, aluminum zirconium pentachlorohydrex, or aluminum zirconium octachlorohydrex is dissolved in water or water solutions of glycols and mixed with a sufficient amount of powdered Betaine. The mixture is stirred at room temperature to obtain the salt, or the solution is dried to remove water to have a powder form of the salt. When Method B is used, a suitable salt to use as a starting material includes various types salts such as aluminum zirconium chlorohydrex, aluminum zirconium chlorohydrex propylene glycol complex, aluminum zirconium chlorohydrex dipropylene glycol complex, and mixtures of any of the foregoing.

Method C: An aqueous aluminum chlorohydrate (ACH) solution made from an activated ACH salt of suitable concentration is mixed with an aqueous solution of zirconyl chloride ($ZrOCl_2$) (or alternatively combining $ZrOCO_3$ and HCl to make the zirconyl chloride in situ) of suitable concentration and powdered Betaine. The mixture is stirred at room temperature for a short period of time and then spray dried to obtain the salt in powder form.

Method D: An aqueous aluminum chlorohydrate (ACH) solution made from an activated ACH salt of suitable concentration is mixed with powdered Betaine. The mixture is stirred at room temperature to obtain a solution of the salt, or the solution is dried to remove water to have a powder form of the salt.

Method E: An aqueous aluminum dichlorohydrate (ADCH) solution made from an ADCH salt of suitable concentration is mixed with powdered Betaine. The mixture is stirred at room temperature to obtain a solution of the salt, or the solution is dried to remove water to have a powder form of the salt.

Method F: An aqueous solution made of zirconyl chloride ($ZrOCl_2$) of suitable concentration is mixed with powdered Betaine. The mixture is stirred at room temperature to obtain a solution of the salt, or the solution is dried to remove water to have a powder form of the salt.

Method G: An alternative procedure for methods A through F uses Betaine hydrochloride as a substitute for Betaine. Accordingly, any of the aqueous solutions of the Al and/or Zr salts described in Methods A–F can be mixed with powdered Betaine hydrochloride. The mixture is stirred at room temperature to obtain a solution of antiperspirant active salt, from which water can be optionally removed in order to obtain a powder.

Examples of commercial salts that may be used in Method B include glycine-free salts such as aluminum zirconium trichlorohydrate, aluminum zirconium tetrachlorohydrate, aluminum zirconium pentachlorohydrate, and aluminum zirconium octachlorohydrate.

If the product is used as a solid powder, the size of the particles of antiperspirant active of the invention currently does not appear to be critical and may include conventional sizes such as in the range of 2 to 100 microns, with selected grades having an average particle size of 30–40 microns; finer sized grades having an average particle size distribution from 2–10 microns with an average size of about 7 microns as made by a suitable dry-grinding method; and micronized grades of the type described in a co-pending patent application U.S. Ser. No. 9/579,322 having an average particle size of less than or equal to 2 microns, particularly less than or equal to 1.5 microns.

The enhanced salts of this invention may be used to formulate antiperspirants having improved efficacy. Such antiperspirants include solids such as sticks and creams (creams sometimes being included in the term "soft solid"), gels, liquids (such as are suitable for roll-on products), and aerosols. The forms of these products may be suspensions or emulsions.

Examples of suitable formulations include the following:

Sticks—Stick products may be made with conventional gelling agents such as stearyl alcohol and dibenzylidene sorbitol. A sample formulation is as follows:
40–55% (particularly 45%) cyclomethicone (especially D5 cyclomethicone)
20–30% (particularly 21%) stearyl alcohol
7–15% (particularly 10%) talc
15–22% (particularly 22%) antiperspirant active in powder form
1–3% (particularly 2%) fragrance Roll Ons—
45–65% (particularly 55%) cyclomethicone (especially D5 cyclomethicone)
0.1–10% (particularly 3%) cyclomethicone/dimethicone copolyol (such as Dow Corning 2-5185 C)
10–25% (particularly 20%) antiperspirant active in solution form (25–45% actives on an anhydrous basis in water)
5–30% (particularly 20%) water
1–3% (particularly 2%) fragrance Soft solids—Soft solids may be made with formulations described in co-pending patent application (U.S. Ser. No. 9/273,152 and PCT Publication WO 99/51192). A sample formulation is as follows:
40–70% (particularly 50%) elastomer in cyclomethicone (KSG-15 from Shin-Etsu)
5–15% (particularly 6%) polyethylene (for example, beads having a density in the range of 0.91–0.98 $g/cm^3$ and an average particle size in the range of 5–40 microns)
10–20% (particularly 15%) C12–15 alkylbenzoate (FINSOLV TN from Finetex)
0.1–25%% (particularly 22%) antiperspirant active in powder form
1–15% (particularly 5%) dimethicone (particularly with a viscosity of 100 centistokes)
1–3% (particularly 2%) fragrance Gels—Gels may be made with a variety of formulations such as
5–50% (particularly 29%) cyclomethicone (particularly D5)
0.1–10% (particularly 3%) cyclomethicone/dimethicone copolyol (such as Dow Corning 2-5185 C)
0–10% (particularly 5%) hydrogenated polyisobutene 250
0–10% (particularly 5%) C12–15 alkylbenzoate (FINSOLV TN from Finetex)
0–10% (particularly 5%) dimethicone (particularly with a viscosity of 100 centistokes)
0.1–25% (particularly 20%) antiperspirant active in powder form or 10–25% (particularly 20%) of active in solution (25–45% actives on an anhydrous basis)
5–50% (particularly 30%) water
1–3% (particularly 2%) fragrance Note that in the explanation of the invention, where water is listed it is intended to count the contribution of the water present in the antiperspirant solution as part of the overall water content. Thus, water is sometimes listed as part of the actives solution or sometimes listed separately.

In a preferred embodiment the refractive indices of the external and internal phases are matched within 0.005 to obtain a clear product.

Particular formulations of interest include:
Formulation A:
0.5–2.5% dimethicone copolyol (for example, Dow Corning 2-5185 C (48%))
55–65% elastomer in cyclomethicone (for example, DC-9040 from Dow Corning Corporation (Midland, Mich.) or KSG-15 from Shin-Etsu Silicones of America (Akron, Ohio))
1–10% PPG-3 myristyl ether
10–25% antiperspirant active of the invention
10–25% water
0.5–1.5% fragrance Formulation B
1.0–3.0% dimethicone copolyol (for example, Dow Corning 2-5185C (48%))
40–60% elastomer in cyclomethicone (for example, DC-9040 from Dow Corning Corporation (Midland, Mich.) or KSG-15 from Shin-Etsu Silicones of America (Akron, Ohio))
1–5% cyclomethicone (in addition to that found in the elastomer)
4–12% PPG-3 myristyl ether
15–30% antiperspirant active of the invention
15–35% water
0.5–1.5% fragrance Formulation C
1.0–3.0% dimethicone copolyol (for example, Dow Corning 2-5185 C (48%))
1–10% hydrogenated polyisobutene (for example, Fancol™ Polyiso 250)

40–55% elastomer in cyclomethicone (for example, DC-9040 from Dow Corning Corporation (Midland, Mich.) or KSG-15 from Shin-Etsu Silicones of America (Akron, Ohio))
3–8% PPG-3 myristyl ether
15–20% antiperspirant active of the invention 20–30% water
1.0–3.0% fragrance
Formulation D
1.0–3.0% dimethicone copolyol (for example, Dow Corning 2-5185 C (48%))
40–60% elastomer in cyclomethicone (for example, DC-9040 from Dow Corning Corporation (Midland, Mich.) or KSG-15 from Shin-Etsu Silicones of America (Akron, Ohio))
3–8% PPG-3 myristyl ether
15–30% antiperspirant active of the invention
15–30% water
0.5–1.5% fragrance
1–10% diethylhexyl naphthalate
Formulation E
0.5–2.5% dimethicone copolyol (for example, Dow Corning 2-5185 C (48%))
60–70% elastomer in cyclomethicone (for example, DC-9040 from Dow Corning Corporation (Midland, Mich.) or KSG-15 from Shin-Etsu Silicones of America (Akron, Ohio))
7–10% antiperspirant active of the invention
25–35% water
1–10% methylpropylene diol (MPDiol)
0.5–1.5% fragrance
Formulation F
1.0–3.0% dimethicone copolyol (for example, Dow Corning 2-5185 C (48%))
6–10% hydrogenated polyisobutene (for example, Fancol™ Polyiso 250)
35–45% elastomer in cyclomethicone (for example, DC-9040 from Dow Corning Corporation (Midland, Mich.) or KSG-15 from Shin-Etsu Silicones of America (Akron, Ohio))
6–10% PPG-3 myristyl ether
40–50% antiperspirant active of the invention as 43% active in water no additional water
0.5–1.0% fragrance
Formulation G
0.1–0.6% dimethicone copolyol (for example, Dow Corning 2-5185 C (48%))
4–7% hydrogenated polyisobutene (for example, Fancol™ Polyiso 250)
40–50% elastomer in cyclomethicone (for example, DC-9040 from Dow Corning Corporation (Midland, Mich.) or KSG-15 from Shin-Etsu Silicones of America (Akron, Ohio))
4–7% PPG-3 myristyl ether
40–50% antiperspirant active of the invention as 43% active in water no additional water
0.5–1.0% fragrance
Formulation H
0.5–2.0% dimethicone copolyol (for example, Dow Corning 2-5185 C (48%))
1–7% hydrogenated polyisobutene (for example, Fancol™ Polyiso 250)
40–50% elastomer in cyclomethicone (for example, DC-9040 from Dow Corning Corporation (Midland, Mich.) or KSG-15 from Shin-Etsu Silicones of America (Akron, Ohio))
45–55% antiperspirant active as 43% active of the invention in water no additional water
0.5–1.5% fragrance
Formulation I
2–7% dimethicone copolyol (for example, Dow Corning 2-5185 C (48%))
0.1–1% Oleath-20
1–5% C12–15 alkyl benzoate (FINSOLV TN)
15–25% elastomer in cyclomethicone (for example, DC-9040 from Dow Corning Corporation (Midland, Mich.) or KSG-15 from Shin-Etsu Silicones of America (Akron, Ohio))
15–25% antiperspirant active
15–30% water
0.5–1.5% fragrance The cosmetic composition according to the present invention can be packaged in conventional containers, using conventional techniques. Where a gel, cream or soft-solid cosmetic composition is produced, the composition can be introduced into a dispensing package (for example, conventional packages for gels with glide on applicators, jars where the gel or cream is applied by hand, and newer style packages having a top surface with pores) as conventionally done in the art. Thereafter, the product can be dispensed from the dispensing package as conventionally done in the art, to deposit the active material, for example, on the skin. For sticks, sprays, aerosols and roll-ons the compositions can be placed in a conventional types of container (with the inclusion of propellants in aerosols). This provides good deposition of the active material on the skin.

Compositions of the present invention can be formulated as clear, translucent or opaque products, although clear products are preferred. A desired feature of the present invention is that a clear, or transparent, cosmetic composition, (for example, a clear or transparent deodorant or antiperspirant composition) can be provided. The term clear or transparent according to the present invention is intended to connote its usual dictionary definition; thus, a clear liquid or gel antiperspirant composition of the present invention allows ready viewing of objects behind it. By contrast, a translucent composition, although allowing light to pass through, causes the light to be scattered so that it will be impossible to see clearly objects behind the translucent composition. An opaque composition does not allow light to pass therethrough. Within the context of the present invention, a gel or stick is deemed to be transparent or clear if the maximum transmittance of light of any wavelength in the range 400–800 nm through a sample 1 cm thick is at least 35%, preferably at least 50%. The gel or liquid is deemed translucent if the maximum transmittance of such light through the sample is between 2% and less than 35%. A gel or liquid is deemed opaque if the maximum transmittance of light is less than 2%. The transmittance can be measured by placing a sample of the aforementioned thickness into a light beam of a spectrophotometer whose working range includes the visible spectrum, such as a Bausch & Lomb Spectronic 88 Spectrophotometer. As to this definition of clear, see European Patent Application Publication No. 291,334 A2. Thus, according to the present invention, there are differences between transparent (clear), translucent and opaque compositions.

EXAMPLES

The following Examples are offered as illustrative of the invention and are not to be construed as limitations thereon. In the Examples and elsewhere in the description of the invention, chemical symbols and terminology have their usual and customary meanings. In the Examples as elsewhere in this application values for n, m, etc. in formulas, molecular weights and degree of ethoxylation or propoxylation are averages. Temperatures are in degrees C. unless otherwise indicated. If alcohol is used, it is 95% unless otherwise indicated. Unless otherwise indicated, "water" or "DI water" mean deionized water. As is true throughout the application, the amounts of the components are in weight percents based on the standard described; if no other standard is described then the total weight of the composition is to be inferred. Various names of chemical components include those listed in the *CTFA International Cosmetic Ingredient Dictionary* (Cosmetics, Toiletry and Fragrance Association, Inc., 7$^{th}$ ed. 1997). While specific amounts of particular elastomers have been described, there are chemical differences in the variety of elastomers that are available. The use of different elastomers may result in the need to increase or decrease the amount of elastomer used in a particular formulation, especially if a clear product is desired.

In the Examples, as elsewhere in the description of the invention, the reference is made to using the antiperspirant active either as a powder or in some type of solution such as dissolved in water at a concentration of 25–45% actives on an anhydrous basis.

In the Examples, the Betaine used is the Betaine of Formula I and the Betaine hydrochloride used is as described in Formula IA.

EXAMPLES

Antiperspirant Salts

Example 1

A salt solution may be made by dissolving 19.26 g $ZrOCl_2 \cdot 8H_2O$ in 49.6 g of water and then adding 8.39 g Betaine anhydrous. After everything is dissolved, an ACH powder (22.65 g of Chlorhydrol from Reheis Chemical Co., Berkeley Heights, N.J.) into the solution with additional DI water so that the total weight of the solution is 100 g. The solution is shaken or stirred to make sure the solution is clear. Optionally, the solution can be spray dried or freeze-dried to make a powder sample. This 30% salt solution (anhydrous basis) has the following composition:

| Al/Zr = 3.5 | Metal/Cl = 1.2 | Betaine/Zr = 1.2 |
|---|---|---|
| Al: | 5.64% | 0.00209 Mole |
| Zr: | 5.45% | 0.000597 Mole |
| Cl: | 7.95% | 0.00224 Mole |
| Betaine | 8.39% | 0.000716 Mole |

Example 2

A salt may solution be made by dissolving 19.26 g $ZrOCl_2 \cdot 8H_2O$ in 49.6 g of water and then adding 5.36 g Betaine anhydrous. After everything is dissolved, an ACH powder (22.65 g of Chlorhydrol from Reheis) into the solution with additional DI water so that the total weight of the solution is 100 g. The solution is shaken or stirred to make sure the solution is clear. Optionally, the solution can be spray dried or freeze-dried to make a powder sample.

This 30% salt solution (anhydrous basis) has the following composition:

| Al/Zr = 3.5 | Metal/Cl = 1.2 | Betaine/Zr = 0.76 |
|---|---|---|
| Al: | 5.64% | 0.00209 Mole |
| Zr: | 5.45% | 0.000597 Mole |
| Cl: | 7.95% | 0.00224 Mole |
| Betaine | 5.36% | 0.000457 Mole |

Example 3

A salt solution may be made by dissolving e 19.26 g of $ZrOCl_2 \cdot 8H_2O$ in 40 gm of distilled water and then adding 9.68 g of Betaine monohydrate. After everything is dissolved, an ACH powder (22.65 g of Chlorhydrol from Reheis) is added to the solution with additional DI water so that the total weight of the solution is 100 g. The solution is shaken or stirred to make sure a clear solution of 30% salt solution (anhydrous basis) is obtained. This 30% salt solution (anhydrous basis) has the following composition:

| Al/Zr = 3.5 | M/Cl = 1.2 | Betaine/Zr = 1.2 |
|---|---|---|
| Al: | 5.64% | 0.00209 Mole |
| Zr: | 5.45% | 0.000597 Mole |
| Cl: | 7.95% | 0.00224 Mole |
| Betaine | 8.39% | 0.000716 Mole |

The solution can be spray dried or freeze-dried to make a powder sample if needed.

Example 4

A salt solution may be made by dissolve 240 g of $ZrOCl_2 \cdot 8H_2O$ in 463 g of distilled water and then adding 100.4 g of Betaine monohydrate. After every thing is dissolved, ACH is added (210 g of ACH Chlorhydrol Powder from Reheis) to the solution. The solution is shaken or stirred to make sure a clear solution of 24% (anhydrous) is obtained. This 24% salt solution (anhydrous basis) has the following composition:

| Al/Zr = 2.6 | Metal/Cl = 1.1 | Betaine/Zr = 1.0 |
|---|---|---|
| Al: | 2.7% | |
| Zr: | 6.9% | |
| Cl: | 6.85% | |
| Betaine | 8.86% | |

The solution can be spray dried or freeze-dried to make a powder sample if needed.

Example 5

A salt solution may be made by mixing 278 g of zirconium hydroxychloride trihydrate solution (15% Zr and 6.66% Cl) with 76 g of Betaine monohydrate at room temperature. After everything is dissolved, ACH is added (400 g of Chlorhydrol Powder solution, which contains 12.3% of Al and 10.0% of Cl) to the solution. The combined solution is shaken or stirred to mix the two solutions well.

The final solution then is spray dried or freeze-dried to make a powder sample. The final powder has the following values:

| Al/Zr = 3.4 | Metal/Cl = 1.4 | Betaine/Zr = 1.2 |
|---|---|---|
| Al: | 14.2% | |
| Zr: | 14.5% | |
| Cl: | 17.2% | |
| Betaine | 22.6% | |

Example 6

Betaine monohydrate powder (286 g) is added to a zirconium compound (1000 g of a 31% solution of zirconium oxychloride ($ZrOCl_2$)) with stirring. Aluminum chlorohydrate ("ACH") (1120 g of a 50% aqueous ACH solution) is then added with additional stirring. The final solution is then diluted with distilled water into an anhydrous concentration of 33.0%, with a Betaine/zirconium molar ratio of 1.45:1; an aluminum/zirconium molar ratio of 3.56:1, and a metal/chloride ratio of 1.01:1.

Example 7

Betaine monohydrate (287 g) is added to a zirconium compound (1000 g of a 31% solution of zirconium oxychloride ($ZrOCl_2$) with stirring. ACH (1204 g of a 50% aqueous ACH solution) is then added with additional stirring. The final solution is then diluted with distilled water into an anhydrous concentration of 30.0% with a Betaine/zirconium molar ratio as 1.45:1; an aluminum/zirconium molar ratio of 3.82:1, and a metal/chloride ratio of 0.98.

Example 8

Betaine monohydrate powder (287 g) is added to a zirconium compound (1000 g of a 31% solution of zirconium oxychloride ($ZrOCl_2$)) with stirring. Aluminum chlorohydrate ("ACH") (2800 g of a 20% ACH solution made from a powder (REACH 101, from Reheis, Berkeley Height, N.J.) is then added with additional stirring. The final solution is then quickly spray dried to remove water. The Zirconium/Aluminum/Betaine ("ZAB") powder obtained has a Betaine/zirconium molar ratio of 1.42:1; an aluminum:zirconium molar ratio of 3.56:1; and a metal:chloride ratio of 1.05:1.

Example 9

A solution of aluminum pentachlorohydrex (Reheis Penta-solv, glycine-free) is prepared by dissolution of 30 g Penta-solv in 62 g of DI water. After the solution is mixed and becomes clear, 8 gm of anhydrous Betaine are added and the solution is mixed at room temperature until clear. The final solution has a Betaine/zirconium molar ratio of 2.83:1; an aluminum/zirconium molar ratio of 9.56:1, and a metal/chloride ratio of 1.67:1.

Example 10

A solution of aluminum octachlorohydrex (Reheis Octa-solv, glycine-free) is prepared by dissolution of 30 g Octa-solv in 62 g of DI water. After the solution is mixed and becomes clear, 8 gm of anhydrous Betaine are added and the solution is mixed at room temperature until clear. The final solution has a Betaine/zirconium molar ratio of 2.65:1; an aluminum/zirconium molar ratio of 8.18:1, and a metal/chloride ratio of 1.40:1.

Example 11

A solution of aluminum chlorohydrex (ACH, Reheis Chlorhydrol, 50%) is prepared by dissolution of 30 g ACH in 62 g of DI water. After the solution is stirred and becomes clear, 8 gm of anhydrous Betaine are added and the solution is mixed at room temperature until clear. The final solution has a Betaine/aluminum molar ratio of 0.25 and an aluminum/chloride ratio of 2.0:1.

Example 12

A solution of aluminum dichlorohydrex (ADCH, Westchlor 100, 38%) is prepared by dissolution of 30 g ADCH in 62 g of DI water. After the solution is mixed and becomes clear, 8 g of anhydrous Betaine is added and the solution is mixed at room temperature until clear. The final solution has a Betaine/aluminum molar ratio of 0.61 and an aluminum/chloride ratio of 1.00.

Example 13

A solution of aluminum chloride hydrate ($AlCl_3$) is prepared by dissolution of 30 g $AlCl_3$ in 62 g of DI water. After the solution is mixed and becomes clear, 8 gm of anhydrous Betaine are added and the solution is mixed at room temperature until clear. The final solution has a Betaine/aluminum molar ratio of 0.30 and an aluminum/chloride ratio of 0.33.

Example 14

A 31% solution of zirconium oxychloride ($ZrOCl_2$) is mixed with 8 g anhydrous Betaine and stirred at room temperature until clear. The final solution has a Betaine/zirconium molar ratio of 0.43 and a zirconium/chloride ratio of 0.50.

Analytical Data for Examples 1, 2 and 10

Size exclusion chromatography ("SEC") or gel permeation chromatography ("GPC") are methods frequently used for obtaining information on polymer distribution in antiperspirant salt solutions. With appropriate chromatographic columns, at least five distinctive groups of polymer species can be detected in a ZAG, appearing in a chromatogram as peaks 1, 2, 3, 4 and a peak known as "5,6". Peak 1 is the larger Zr species (greater than 60 Angstroms). Peaks 2 and 3 are larger aluminum species. Peak 4 is the smaller aluminum species (aluminum oligomers) and has been correlated with enhanced efficacy for both ACH and ZAG salts. Peak 5,6 is the smallest aluminum species. The relative retention time ("Kd") for each of these peaks varies depending on the experimental conditions. This method is also applicable to ZAB salts. Data for Table A was obtained using the SEC method described in an issued patent owned by the same company as a this case, U.S. Pat. No. 6,066,314, incorporate by reference as to the test method described therein.

TABLE 1

SEC Polymer distribution of the ZAB sample 1 from Example 1 at room temperature.

| Time (days) | Peak1/All Peaks |
|---|---|
| 8 | 0.003 |
| 15 | 0.008 |
| 31 | 0.001 |
| 70 | 0.039 |
| 86 | 0.070 |
| 122 | 0.086 |
| 146 | 0.152 |
| 192 | 0.206 |
| 294 | 0.163 |

TABLE 2

SEC Polymer distribution of the ZAB sample 1 from Example 1 at 40 degree C.

| Time (days) | Peak1/All Peaks |
| --- | --- |
| 8 | 0.027 |
| 15 | 0.070 |
| 31 | 0.121 |
| 70 | 0.148 |
| 86 | 0.144 |
| 129 | 0.185 |
| 146 | 0.168 |

TABLE 3

SEC Polymer distribution of the ZAB sample 1 from Example 2 at room temperature.

| Time (days) | Peak1/All Peaks |
| --- | --- |
| 8 | 0.098 |
| 15 | 0.146 |
| 31 | 0.196 |
| 70 | 0.227 |
| 86 | 0.251 |
| 122 | 0.283 |
| 146 | 0.315 |
| 192 | 0.400 |
| 294 | 0.363 |

TABLE 4

SEC Polymer distribution of the ZAB sample 1 from Example 2 at 40 degree C.

| Time (days) | Peak1/All Peaks |
| --- | --- |
| 8 | 0.270 |
| 15 | 0.260 |
| 31 | 0.311 |
| 70 | 0.307 |
| 86 | 0.342 |
| 129 | 0.365 |
| 146 | 0.349 |

TABLE 5

SEC Polymer distribution of the ZAB sample 1 from Example 10 at room temperature.

| Time (days) | Peak1/All Peaks |
| --- | --- |
| 4 | 0.214 |
| 24 | 0.199 |
| 45 | 0.191 |
| 80 | 0.193 |
| 108 | 0.190 |

Example 15

General Method for Making Antiperspirant Products

In general, the external and internal phases are formed separately either at room temperature or with heating as described below. The internal phase is added to the external phase very slowly while stirring at to form an emulsion. After the addition has been completed, the mixture is stirred at higher speed to achieve a homogeneous mixture. The final formula viscosity is then achieved by homogenizing the emulsion under either batch or continuous process conditions as described below. The fragrance may be added at any time during the process prior to final homogenization.

Preparation of the External Phase:

The ingredients to be used in the external phase (including the elastomer) are weighed out at room temperature and combined in a suitable vessel such as a 2 liter glass beaker. The mixture is stirred at about 500 rpm for 15–20 minutes using an overhead mixer such as a Lightnin' Mixer Model L1003. If a waxy or solid emollient is to be added to the external (also called "continuous") phase, the mixture may be heated to facilitate dissolution while stirring then cooled to room temperature prior to combination with the internal phase as described below. If an elastomer component used it is obtained as a suspension of elastomer in cyclomethicone (for example at a concentration of 6% active in D5 cyclomethicone). The elastomer component is added to the external phase with stirring at high speed (500–700 rpm for a 0.5 kilogram batch) until no particles of elastomer are visible to the eye.

Preparation of the Internal Phase:

The internal dispersed phase is prepared as described below. Ingredients are mixed for a time sufficient to achieve homogeneity. The antiperspirant active used is weighed into a large beaker equipped with an overhead stirrer. Other internal phase ingredients are then added while stirring.

The fragrance (if any is used) is added last and may be added either to the internal phase or the external phase or the final formula prior to homogenization. For many of the examples described here, one could add the fragrance to the internal phase.

If an optional non-ionic emulsifier such as Oleath-20 is used, the emulsifier and propylene glycol are combined in a separate beaker and heated to 40 degrees C. with stirring until the non-ionic emulsifier completely dissolved. The heat is turned off and the remaining ingredients to be used in the internal phase, including the antiperspirant active are weighed out and added to the mixture of propylene glycol and non-ionic emulsifier.

If water or a salt solution is used, the internal phase is prepared as follows. The solution containing antiperspirant active salt as received from supplier is weighed into a large beaker equipped with a magnetic stirrer. Additional ingredients such as propylene glycol, ethanol and water are added while stirring. If a salt water solution is used (such as for NaCl, etc.), the salt water solution is prepared by dissolving the crystalline salt in water in a separate beaker and stirring until dissolved. The salt water solution is then added to the rest of the internal phase and the mixture is stirred until homogeneous.

Preparation of the Emulsion:

The internal phase made as described above is then added to the external phase over the course of 15–30 minutes while stirring at a speed of 500–700 rpm. After the addition is complete, the mixture is stirred at 500–700 rpm for 20 minutes using a Lightnin Mixer Model L1003. The mixture is then homogenized for 2–4 minutes (especially 3 minutes) using a homogenizer from Greerco Corp., Hudson, N.H. at a reading of about 60 on a Powerstat Variable Autotransformer from Superior Electric Co., Bristol, Conn.

Further Processing:

The product is then further processed by homogenization to achieve the desired final viscosity. This can be done by using a Gilford-Wood Model 1-L (Greerco Corp., Hudson, N.H.) homogenizer. The homogenizer speed is controlled by a Powerstat Variable Autotransformer Type 3PN116B (Superior Electronic. Co., Bristol, Conn.). Typical voltage setting and processing time are chosen to give a desired final formula viscosity.

An other method of homogenization of the final product is to pass the emulsion through a colloid mill such as a Sonic Tri-Homo Colloid Mill or a process sonolator such Sonic Production Sonolator 200–30 both available from Sonic Corporation of Stratford, Conn. Process conditions are chosen to give the desired final product viscosity.

Examples 16–36

Compositions Based on Example 15

The methods described in Example 15 may be used to make the products listed in Tables 6 and 7 with the types and amounts of ingredients listed in the Tables 6 and 7. Amounts are in percent by weight based on the total weight of the composition.

TABLE 6

| Ingredient | Ex. 16 | Ex. 17 | Ex. 18 | Ex. 19 | Ex. 20 | Ex. 21 | Ex. 22 | Ex. 23 | Ex. 24 | Ex. 25 |
|---|---|---|---|---|---|---|---|---|---|---|
| External Phase | | | | | | | | | | |
| Elastomer (KSG-15, 6% active) | 62 | 50 | 48 | 40 | 41.5 | 42.0 | 46.5 | 35 | 32.17 | 25 |
| Dimethicone copolyol (Dow Corning 2-5185, 48% active in cyclomethicone) | 2 | 2 | 1.5 | 4 | 1.5 | 0.5 | 1.0 | 1.0 | 2.48 | 1.0 |
| Hydrogenated polyisobutene (Polyiso 250) | 0 | 0 | 5 | 8 | 5 | 5 | 5 | 5 | 4.95 | 0 |
| PPG-3 Myristyl Ether | 5 | 5 | 4.5 | 0 | 4.5 | 5.0 | 0 | 0 | 0 | 5 |
| C12–15 alkyl benzoate (FINSOLV TN) | — | — | — | 2.0 | — | — | — | — | — | — |
| Cyclomethicone (Dow Corning 245) | 0 | 2 | 0 | 0 | 0 | 0 | 0 | 0 | 0 | 0 |
| Fragrance | 1 | 1 | 1 | 1 | 1 | 1 | 1 | 1 | 1 | 0 |
| Internal Phase | | | | | | | | | | |
| Antiperspirant Active[a] | 15 | 20 | 17.5 | 19.5 | 46.5 | 46.5 | 46.5 | 58 | 59.40 | 48.45 |
| Water (deionized)[b] | 15 | 20 | 22.5 | 25 | 0 | 0 | 0 | 0 | 0 | 0 |
| Oleath-20 (HLB > 8) | 0 | 0 | 0 | 0.5 | 0 | 0 | 0 | 0 | 0 | 19.55 |
| Total | 100 | 100 | 100 | 100 | 100 | 100 | 100 | 100 | 100 | 100 |

[a]Any of the actives described in Examples 1–14 may be used.
[b]Note that in the examples, sometimes the antiperspirant active is listed as a solution (which will include a water component) under the "active" designation with little or no water and sometimes the active and water are listed separately.

TABLE 7

| Ingredient | Ex. 26 | Ex. 27 | Ex. 28 | Ex. 29 | Ex. 30 | Ex. 31 | Ex. 32 | Ex. 33 | Ex. 34 | Ex. 35 | Ex. 36 |
|---|---|---|---|---|---|---|---|---|---|---|---|
| External Phase | | | | | | | | | | | |
| Elastomer (DC 9040) 12% active) | 55 | 62 | 62 | 40 | 41.5 | 25 | 31.5 | 21 | 17 | 17 | 50 |
| Dimethicone copolyol (Dow Corning 2-5185, 48% active in cyclomethicone) | 1 | 2 | 2 | 4 | 1 | 1 | 2.5 | 1 | 1 | 1 | 2 |
| Hydrogenated polyisobutene (Polyiso 250) | 5 | — | — | 8 | 5 | — | 5 | 1.5 | 1.5 | 1.5 | — |
| PPG-3 Myristyl Ether | 3 | 4.5 | 5 | — | 5 | 5 | — | 0.5 | 0.5 | 0.5 | 5.0 |
| C12–15 alkyl benzoate (FINSOLV TN) | — | — | — | 2 | — | — | — | — | — | — | — |
| Cyclomethicone (Dow Corning 245) | — | — | — | — | — | — | — | 5 | 9.0 | 9.0 | 2.0 |
| Fragrance | 1 | 1 | 1 | 1 | 1 | 1 | 1 | 1 | 1 | 1 | 1 |
| Internal Phase | | | | | | | | | | | |
| Antiperspirant Active[a] | 15 | 15.5 | 30 | 19.5 | 46.5 | 48.45 | 60.0 | 60.5 | 63.68 | 60.13 | 20 |
| Water (deionized)[b] | 20 | 15 | — | 25 | — | 19.55 | — | 9.5 | 6.32 | 9.87 | 20 |
| Oleath-20 (HLB > 8) | — | — | — | 0.5 | — | — | — | — | — | — | — |
| Total | 100 | 100 | 100 | 100 | 100 | 100 | 100 | 100 | 100 | 100 | 100 |

[a]See explanation of actives used. Actives according to Examples 1–14 may be used.
[b]Note that in the examples, sometimes the antiperspirant active is listed as a solution (which will include a water component) under the "active" designation with little or no water and sometimes the active and water are separately listed

Examples 37–39

(Betaine Hydrochloride)

The processes described in the previous examples may be used with the substitution of Betaine hydrochloride for Betaine to the extent that any of the aqueous solutions of the Al and/or Zr salts can be mixed with powdered Betaine hydrochloride. The mixture is stirred at room temperature to obtain a solution of AP active salt, from which water can be optionally removed in order to obtain a powder. Several detailed examples using Betaine hydrochloride are presented below.

Example 37

A salt solution may be made by dissolving 18.15 g $ZrOCO_3 \times 8H_2O$ in 5.95 g of concentrated HCl (37%) and 20 g of water (such as deionized ("DI") water). After a clear solution is formed, 9.17 gm of Betaine hydrochloride is added and stirred until dissolved. Subsequently, 22.65 g of ACH powder (Chlorhydrol from Reheis Chemical Co., Berkeley Heights, N.J.) is added into the solution with additional DI water so that the total weight of the solution is 100 g. The solution is shaken or stirred to make sure the solution is clear. Optionally, the solution can be spray dried or freeze-dried to make a powder sample.

This 30% salt solution (anhydrous basis) has the following composition:

| Al/Zr = 3.5 | M/Cl = 1.2 | Betaine/Zr = 1.0 |
|---|---|---|
| Al: | 5.64% | 0.00209 mole |
| Zr: | 5.45% | 0.000597 mole |
| Cl: | 7.95% | 0.00224 mole |
| Betaine | 7.00% | 0.000597 mole |

Example 38

A salt solution may be made by dissolving 19.26 g $ZrOCl_2 \cdot 8H_2O$ in 49.6 g of water and then adding 8.39 g Betaine hydrochloride. After everything is dissolved, an ACH powder (22.65 g of Chlorhydrol from Reheis Chemical Co., Berkeley Heights, N.J.) is added into the solution with additional deionized water so that the total weight of the solution is 100 g. The solution is shaken or stirred to make sure the solution is clear. Optionally, the solution can be spray dried or freeze-dried to make a powder sample.

Example 39

A salt solution may be made by dissolving 19.26 g $ZrOCl_2 \cdot 8H_2O$ in 47.0 g of water and then adding 11.0 g Betaine hydrochloride. After everything is dissolved, an ACH powder (22.65 g of Chlorhydrol from Reheis Chemical Co., Berkeley Heights, N.J.) is added into the solution with additional deionized water so that the total weight of the solution is 100 g. The solution is shaken or stirred to make sure the solution is clear. Optionally, the solution can be spray dried or freeze-dried to make a powder sample.

We claim:

1. A glycine-free aluminum and/or zirconium Betaine salt having a metal to chloride molar ratio in the range of 0.3–2.5:1, a Betaine:aluminum molar ratio in the range of 0.05–1.0:1 and/or a Betaine:zirconium molar ratio in the range of 0.2–3.0:1, wherein the Betaine has the following Formula I:

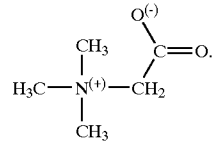

Formula I wherein the glycine-free aluminum and/or zirconium Betaine salt comprises a starting material selected from the group consisting of aluminum salts, zirconium salts, and aluminum/zirconium salts, and wherein if the salt comprises an aluminum only salt, it is selected from the group consisting of aluminum chloride, aluminum chlorohydrate and aluminum dichlorohydrate.

2. A salt according to claim 1 wherein the metal to chloride molar ratio is in the range of 0.9–2.1:1.

3. A salt according to claim 1 comprising aluminum and wherein the Betaine:aluminum molar ratio is in the range of 0.05–0.26:1.

4. A salt according to claim 1 comprising aluminum and wherein the Betaine:aluminum molar ratio is in the range of 0.05–0.16:1.

5. A salt according to claim 1 comprising zirconium and wherein the Betaine:zirconium molar ratio is in the range of 0.4–1.5:1.

6. A salt according to claim 3 or claim 4 comprising zirconium and wherein the Betaine:zirconium molar ratio is in the range of 0.4–1.5:1.

7. An antiperspirant and/or deodorant product made with a salt according to any one of claims 1, 2, 3, 4 or 5.

8. A stick antiperspirant and/or deodorant comprising:
   40–55% cyclomethicone; 20–30% stearyl alcohol; 7–15% talc; 15–22% of a salt according to claim 1 added in powder form; and 1–3% fragrance.

9. A roll-on antiperspirant and/or deodorant comprising:
   45–65% cyclomethicone; 0.1–10% cyclomethicone/dimethicone copolyol; 10–25% of a salt according to claim 1 in a solution as 25–45% actives on an anhydrous basis in water; 5–30% water; and 1–3% fragrance.

10. A soft solid antiperspirant and/or deodorant comprising: 40–70% elastomer in cyclomethicone; 5–15% polyethylene beads having a density in the range of 0.91–0.98 g/cm³ and an average particle size in the range of 5–40 microns; 10–20% C12–15 alkylbenzoate; 0.1–25% of a salt according to claim 1 added in powder form; 1–15% dimethicone; and 1–3% fragrance.

11. A gel antiperspirant and/or deodorant comprising:
   5–50% cyclomethicone; 0.1–10% cyclomethicone/dimethicone copolyol; 0–10% hydrogenated polyisobutene 250; 0–10% C12–15 alkylbenzoate; 0–10% dimethicone; 0.1–25% of a salt according to claim 1 added in powder form or as 10–25% of active in solution (25–45% actives on an anhydrous basis); 5–50%; and 1–3% fragrance.

12. A process for making the salt of claim 1 comprising combining a glycine-free aluminum and/or zirconium salt with a Betaine of Formula I or a Betaine hydrochloride of Formula IA:

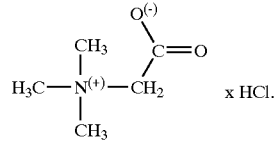

Formula IA

* * * * *